United States Patent [19]

Arlinghaus, Jr.

[11] Patent Number: 5,579,378
[45] Date of Patent: Nov. 26, 1996

[54] MEDICAL MONITORING SYSTEM

[76] Inventor: Frank H. Arlinghaus, Jr., Windmill La., Rumson, N.J. 07760

[21] Appl. No.: 533,167

[22] Filed: Sep. 25, 1995

Related U.S. Application Data

[63] Continuation-in-part of Ser. No. 111,630, Aug. 25, 1993, abandoned.

[51] Int. Cl.⁶ .................................................. H04M 11/00
[52] U.S. Cl. ...................... 379/106; 379/90; 364/413.02; 128/904
[58] Field of Search .................................. 379/38, 45, 49, 379/42, 52, 106, 107, 102, 104, 93, 97–99; 128/670, 904; 395/500; 364/413.02

[56] References Cited

U.S. PATENT DOCUMENTS

| | | |
|---|---|---|
| 3,726,270 | 4/1973 | Griffis et al. . |
| 3,872,253 | 3/1975 | Jurschak . |
| 3,896,792 | 7/1975 | Vail et al. . |
| 4,006,461 | 2/1977 | Coulter et al. . |
| 4,034,743 | 7/1977 | Greenwood et al. . |
| 4,296,756 | 10/1981 | Dunning et al. . |
| 4,528,422 | 7/1985 | Cupani . |
| 4,531,527 | 7/1985 | Reinhold . |
| 4,608,686 | 8/1986 | Barsellotti . |
| 4,685,123 | 8/1987 | Hsia et al. . |
| 4,741,022 | 4/1988 | Chebra et al. . |
| 4,838,275 | 6/1989 | Lee . |
| 5,161,222 | 11/1992 | Montejo . |
| 5,369,691 | 11/1994 | Cain et al. . |

*Primary Examiner*—Wing F. Chan
*Attorney, Agent, or Firm*—Hoffmann & Baron

[57] ABSTRACT

A medical monitoring system which includes at least one patient medical monitoring apparatus for monitoring at least one aspect of a patient's physical condition and generating at least one variable signal in response to the monitoring. The system includes at least one station distributor electrically connected to the at least one patient medical monitoring apparatus and to a first end of a telephone line. A system distributor is electrically connected to a second end of a telephone line and to at least one system monitoring apparatus. The at least one station distributor receives each of the at least one variable signals and generates an information signal therefrom. The information signal is transmitted to the system distributor where monitoring information contained within the information signal is retrieved and distributed to the at least one system monitoring apparatus without interrupting normal telephone operation.

20 Claims, 5 Drawing Sheets

MEDICAL MONITORING SYSTEM

BACKGROUND OF THE INVENTION

This is a continuation-in-part of application Ser. No. 08/111,630, filed on Aug. 25, 1993, now abandoned.

The present invention relates to medical monitoring, and more particularly relates to a system to continuously, or at operator discretion, monitor information provided by at least one patient medical monitoring apparatus using an active telephone line.

Medical monitoring systems known to date monitor at least some aspect of a patient's physical condition and generate monitoring information therefrom. The medical monitoring information may be a continuous signal, such as that generated by a heart rate or respiratory rate monitor or a signal delivered at deliberate intervals to provide active patient monitoring. In many circumstances, medical monitoring efficiency is improved by monitoring information from one or multiple medical monitoring apparatus and providing the pooled information to a central location for disseminating the same. Accordingly, electrical wires or cables are required to electrically couple the pooled monitoring information from the medical monitoring apparatus to the central location.

Extending electrical wires or cables from a medical monitoring apparatus to a central location creates several problems which are particularly troublesome in treatment centers such as a hospital. Multiple electrical wires and cables consume valuable space for conduits which is at a premium in most hospital settings. Electrical wires and cables, therefore, must be positioned to avoid interfering with hospital staff and patient administration. Substantial cost is incurred in cable installation and reinstallation to accomplish cable positioning to avoid or minimize such interference. Problems of crosstalk, i.e., erroneous signals induced in closely positioned electrical wires and cables, may also arise when routing and grouping multiple wires or cables.

Several attempts have been made to utilize existing telephone lines to minimize the amount of electrical wire and cabling required for information transfer. For example, U.S. Pat. No. 4,838,275 discloses a home medical surveillance system for monitoring a patient's condition and transmitting signals indicating the same to a central monitoring location via a telephone line. The system utilizes an apparatus to convert data from medical monitoring devices for transmission via a modem over a telephone line to a control office. Data may also be transmitted from the control office to the medical devices via the same telephone line. Each control office within the system, however, requires a dedicated data line for data communication and a dedicated voice line for voice communication, that is, two separate telephone lines for communication.

Outside of the medical field, several signal transmission and surveillance systems use existing telephone lines to minimize the number of electrical wires and cabling inherent for use in monitoring one or more surveillance apparatus. For example, U.S. Pat. No. 3,872,253 to Jurschak discloses a monitoring system which utilizes a system user's telephone line. The system includes a user unit at the user's location that transmits a modulating current signal defining the status of an event to a central monitoring location during normal telephone operation. The central monitoring location receives the modulating current signal from the user unit where it is 180° phase-shifted and retransmitted onto the telephone line canceling the effect of the modulating current signal. The absence/presence of the modulating signal corresponds to an alarm/no alarm condition. The system is incapable of transferring sophisticated communication information, such as would be required with respect to a plurality of medical monitoring apparatus which may be connected to a patient. Furthermore, there is no teaching in this reference for multiple point transmission of data over existing telephone lines.

U.S. Pat. No. 4,528,422 also discloses a monitoring system which uses existing telephone lines. The system includes at least one device for monitoring local conditions and transmitting signal information indicating the same through a balanced modem via telephone ring and tip lines to a processing station. The balanced modem provides a frequency shift keyed digital signal with balanced phase and amplitude whereby the signal on the ring line cancels the signal on the tip line at a receiving telephone. Each processing station may be coupled via telephone lines to a central station which monitors all processing stations within the system. Although signal transmission is transparent to telephone users, the balanced modem may load the telephone lines, creating a 3 dB drop in voice signal level.

U.S. Pat. No. 4,531,527 to Reinhold discloses a medical monitoring system which includes a patient unit for monitoring a patient. The monitored information is transmitted via an existing telephone line to a physician's office using a modem. The patient unit is used to record the monitored information. The recorded information is transmitted to the physician's office by the modem for analysis by the physician. The Reinhold patent does not discuss a system for the input of multiple signals from a plurality of bedsides for transmission over existing telephone lines to a distributing means so that the information may be distributed to any number of a specific system monitoring apparatus.

U.S. Pat. No. 4,741,022 discloses a monitoring system utilizing existing telephone lines. Monitoring units located at user premises transmit frequency shift keyed (FSK) signals below the audible frequency range via a telephone line to a central control unit (CCU). Each FSK signal indicates to the CCU that the monitoring units are in a no alarm state, transparent to a telephone user. A problem arises, however, if an alarm condition occurs. During an alarm condition, the CCU detects a break in the FSK signal transmitted from a monitoring unit. The CCU responds by interrogating the monitoring unit in the audible frequency range. This is regardless of whether or not the subscribers phone line is in use (i.e., off-hook operation), interrupting conversation.

It is therefore an object of the present invention to provide a medical monitoring system which uses existing telephone lines to transmit continuous medical monitoring information to a monitoring station without interrupting or interfering with normal telephone operation.

It is another object of the present invention to provide a medical monitoring system that uses existing telephone lines to transmit continuous medical monitoring information generated by a plurality of medical monitoring apparatus without interrupting or interfering with normal telephone operation.

It is still another object of the present invention to provide a medical monitoring system that uses an existing telephone line to transmit continuous medical monitoring information to a monitoring station thereby avoiding the need for installing electrical wires and cabling to transmit the same.

It is yet another object of the present invention to provide a medical monitoring system in which information from a plurality of medical monitors which are monitoring a patient's condition can be encoded and transmitted via pre-existing telephone lines to a system distributing network capable of decoding the .encoded signal and directing the signals to any of a plurality of system monitoring apparatus.

SUMMARY OF THE INVENTION

The present invention, which addresses the needs of the prior art, provides a system for communicating medical monitoring information over existing telephone lines without interrupting normal telephone operation. The system consists of a combination of several elements including at least one patient medical monitoring apparatus which continuously, or at operator discretion, monitors at least one aspect of physical condition of a patient and generates a variable output signal representing the condition. The patient medical monitoring apparatus is electrically connected to at least one station distributing means which is connected to a first end of a telephone line.

The medical monitoring system also includes a system distributing means electrically connected to a second end of the telephone line and at least one system monitoring apparatus electrically connected to the system distributing means via another telephone line. The at least one station distributing means receives each of the at least one variable signal and generates an information signal therefrom. The information signal also includes operator input routing information to provide a destination for the medical monitoring information. The composite information signal is then transmitted at a frequency outside the audio baseband to the system distributing means over the pre-existing telephone line where monitoring information contained within the information signal is distributed to the at least one system monitoring apparatus without interrupting normal telephone operation.

The at least one station distributing means within the medical monitoring system may include means for modulating the at least one variable signal thereby forming the information signal. The system distributing means may include means for demodulating the information signal and forming separate signal components.

The system distributing means may also receive input data from a user or system monitoring device, modulating the data to form a data signal and transmitting the same to the station distributing means, the station distributing means including means for demodulating the data signal and retrieving the data therefrom and distributing the data. The station distributing means may include means for receiving user input, modulating the user input to form an input signal and transmitting the same to the system distributing means. It follows that the system distributing means includes means for demodulating the input signal to retrieve the user input and distributing the same. In this manner, a system user monitoring a physical condition of a patient at a central location not only receives but may provide input for use by the medical monitoring apparatus establishing two-way continuous communication via the existing telephone line. The system distributing means also includes means for sorting, prioritizing and directing the information signal based upon the frequency or routing information contained herein.

As a result of the process and apparatus of the present invention, medical monitoring may now be performed without the inconvenience of extending additional wires or cables between a medical monitoring apparatus and system monitoring means, i.e., pre-existing telephone lines are used.

Medical monitoring information may now be transferred two ways over existing telephone lines without disturbing normal telephone communication occurring thereon. Because of the unique process by which the medical monitoring system transmits medical monitoring information over an existing telephone line, multiple medical monitoring apparatus can transmit multiple signals over the telephone line in lieu of dedicated electrical wires or cables resulting in considerable savings of time and money.

DETAILED DESCRIPTION OF THE INVENTION

Figure 1:
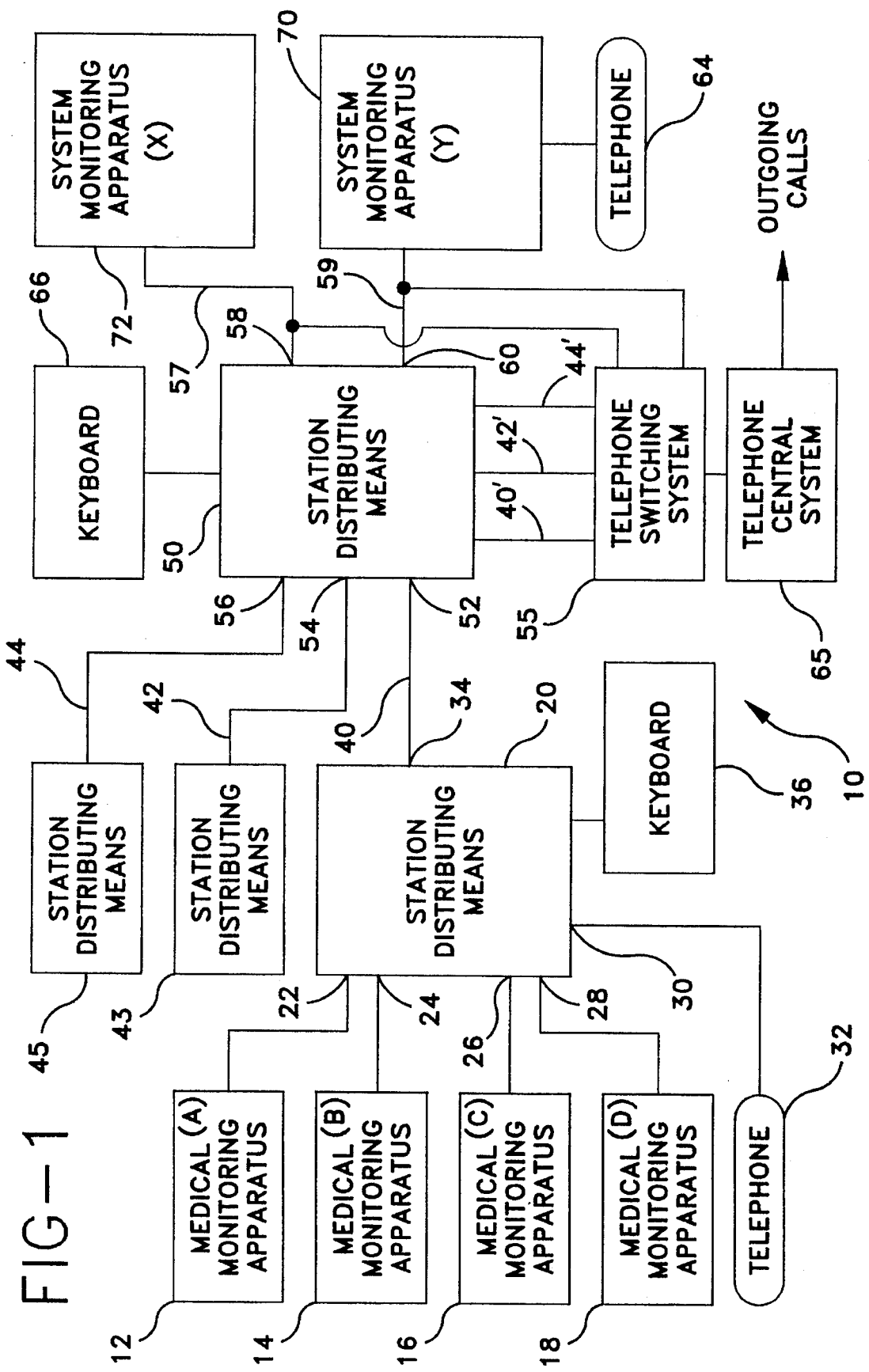
FIG. 1 is a block diagram of a medical monitoring system of the present invention.

One embodiment of a medical monitoring system 10 of the present invention is shown in FIG. 1. The medical monitoring system 10 includes four medical monitoring apparatus 12, 14, 16, 18, designated A, B, C, and D, respectively. Each medical monitoring apparatus is electrically connected to receiver ports 22, 24, 26 and 28 of a station distributing means 20. Each medical monitoring apparatus continuously monitors at least one aspect of a patient's physical condition and generates a variable signal representing the monitored condition. The variable signal may or may not be continuous. It should be noted that the medical monitoring system 10 is not limited to four monitoring apparatus as shown in FIG. 1, but may be customized to accommodate from one to a great many medical monitoring apparatus.

The station distributing means 20 receives the variable signals from each medical monitoring apparatus A, B, C, D and modulates each variable signal to a distinct frequency preferably outside of the audio base band. The station monitoring means may perform modulation of the variable signal using any known frequency modulation means to modulate the signal to a frequency beyond the audio baseband. More specifically, the station distributing means 20 combines each modulated signal corresponding to the output of each medical monitoring apparatus and generates a mixed signal in response thereto. The mixed signal is dispatched from transmission port 34 of the station distributing means 20 to a first end of a pre-existing telephone line 40.

A telephone 32, normally directly connected to telephone line 40 through a phone jack (not shown), may be electrically connected to a first end of telephone line 40 through station distributing means 20. The station distributing means includes a receptacle (not shown) that functions as a phone jack for electrical connection to the telephone. Because the variable signal components generated within each medical monitoring apparatus are modulated outside the audio baseband, normal telephone communication is not disturbed by the transmission of medical monitoring information over the pre-existing telephone line.

A keyboard 36 or other means for inputting data for transmission may be also electrically connected to the station distributing means 20. The keyboard or other means allows a user to insert user information within the mixed signal, such as routing information or source identifying signals. The routing information enables the operator to encode the mixed signal for routing by the system distributing means to a specified system monitoring apparatus. The routing information may be inputted to encode all information provided by medical monitoring apparatus to a station distributing means to be routed to a single system monitoring apparatus, or, in the alternative, may encode, for example, all heart rate monitors to be directed to a central location. Furthermore, the routing information may include a phone number so that any portion of the mixed signal may be routed to any location, including, for example, a doctor's office who cannot be present at a patient's bedside or at the hospital. Thus, the system would be compatible both within a hospital setting, and also outside the hospital setting, for example, to transmit medical monitoring information from a patient's home to a doctor's office. Lastly, the routing information will enable the medical monitoring apparatus of the present invention to have multiple targets for the information contained in the mixed signal formed by the station monitoring means. The source identifying signals may be used to identify a specific medical monitoring apparatus which identifying signal may also be used to direct the information therefrom. For example, the system distributing means may be programmed to direct all heart monitor information from a plurality of station monitoring means to a central observation station. As with the variable signal components, the user information is modulated by a carrier frequency outside the audio frequency range.

A system distributing means 50 is electrically connected to a second end of telephone line 40 through a port 52. In a preferred embodiment, the system distributing means 50 is connected in parallel to a telephone switching system 55 as a private branch exchange (PBX) of a hospital telephone system. The telephone switching system 55 is in turn connected to a telephone central office for routing of outgoing calls either locally or long distance. System distributing means 50 receives the mixed information signal transmitted from each station distributing means 20, and demodulates the mixed signal into its signal components, including the routing information and medical monitoring information. The system distributing means 50 then separates and distributes the demodulated mixed signal components in accordance with the routing information contained therein. Additional station distributing means may be coupled through telephone lines 42, 44 connected to the system distributing means 50, at, for example, ports 54 and 56, respectively. The system distributing means is, in effect, a hybrid telephone switching system.

Two system monitoring devices 72 and 70, designated as X and Y, respectively, are electrically connected to output ports 58, 60 of system distributing means 50, respectively, via pre-existing telephone lines 57, 59. The demodulated mixed signal components may be distributed by system distributing means 50 to either or both system monitoring devices 70 and 72 depending upon the routing information or source identifying signal. The monitoring information contained within each signal component may be displayed by each system monitoring apparatus or may be processed further therein. The system monitoring devices, 70, 72 may comprise any means known to those skilled in the art for receiving and displaying or processing of continuous medical monitoring information. For example, a display, a micro-computer with a display, a facsimile device, and an information storage or data processing device may receive and display such medical monitoring information.

Figure 2:
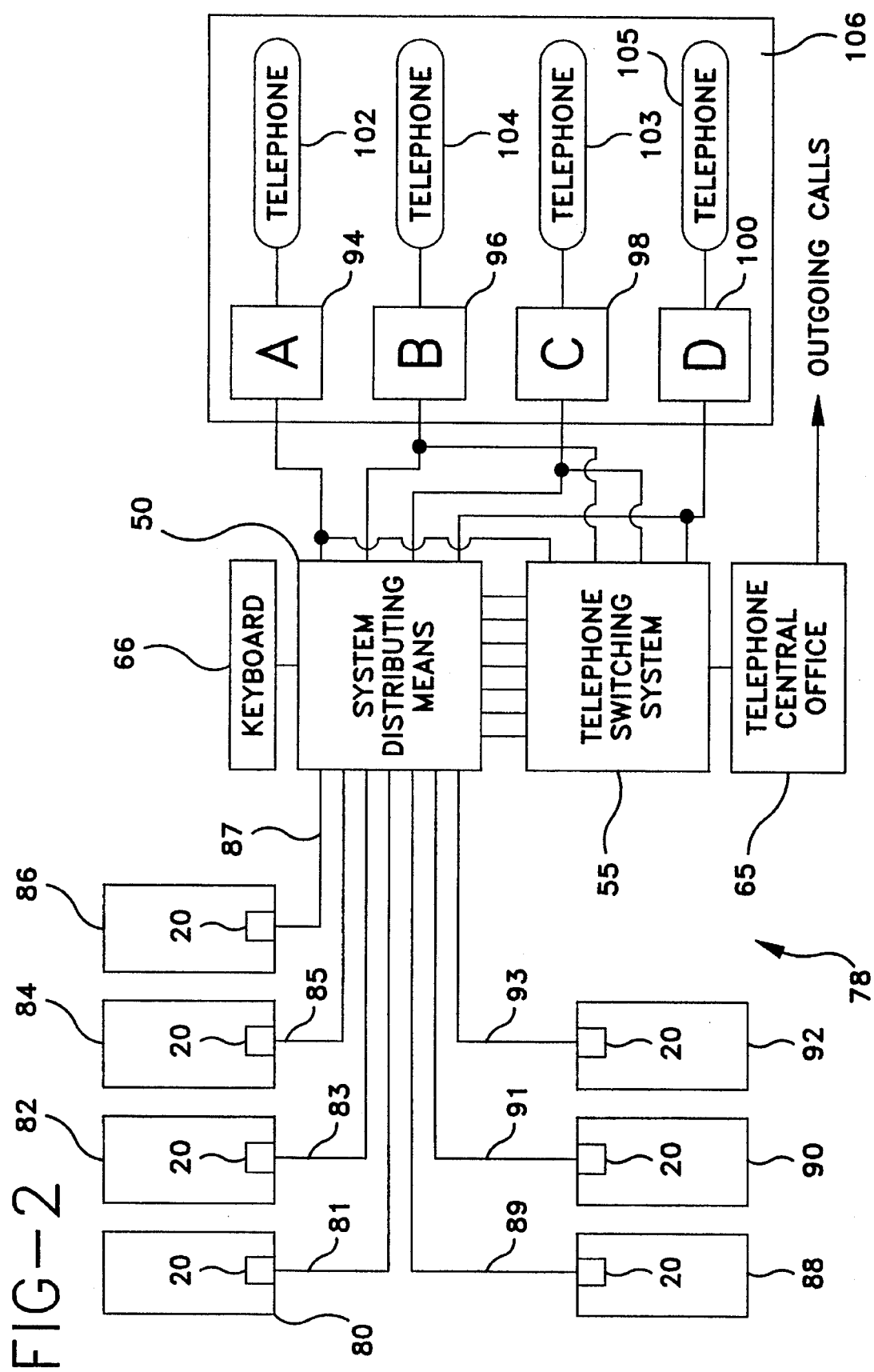
FIG. 2 is a block diagram of another embodiment of the medical monitoring system of the present invention.

At least one telephone 64 may be electrically connected to telephone line 59 through system monitoring apparatus 70. It is possible to have a telephone located at each system monitoring apparatus station as shown in FIG. 2. A keyboard 66, or other data inputting means, may be electrically connected to system distributing means 50 to input data thereto. System distributing means 50 modulates the data thereby forming a data signal. The data signal may then be distributed to one or all station monitoring apparatus 12, 14, 16 and 18 over telephone line 40. Station distributing means 20 demodulates the data signal and distributes the demodulated data signal components to any or all of medical monitoring apparatus A, B, C and D.

The medical monitoring system 10 of the present invention is ideal for use in a hospital environment. For example, hospital wings directed towards specific treatments of particular maladies, such as a cardiac care unit, at times require many of the same medical monitoring apparatus for treating multiple patients in multiple hospital rooms. Particularly within a cardiac care unit, each patient under care will be monitored by multiple cardiac medical monitoring devices. To employ a separate electrical cable between each medical monitoring apparatus and central monitoring location would amount to a considerable financial burden, in addition to the valuable hospital space required to route each cable. Utilizing the telephone lines of an existing communication system already in place within the hospital or hospital wing in lieu of installing a new separate cable for each monitoring apparatus results in considerable savings.

FIG. 2 shows another embodiment of a medical monitoring system 78 of the present invention. The medical monitoring system 78 is incorporated within a telephone system present within a wing of a hospital allowing the use of existing telephone lines 81, 83, 85, 87, 88, 91 and 93. The medical monitoring system 78 includes seven hospital rooms 80, 82, 84, 86, 88, 90 and 92, each containing a station distributing means 20, to which is connected a plurality of medical monitoring apparatus 12, 14, 16, 18, and a telephone 36 (FIG. 1). Accordingly there are seven medical monitoring apparatus A, seven medical monitoring apparatus B, seven medical monitoring apparatus C and seven medical monitoring apparatus distributed throughout each the seven hospital rooms.

Data in the form of a variable monitoring signals is generated within each of these four separate type medical monitoring apparatus A, B, C, D. The variable monitoring signals are transferred to each of the seven station distributing means 20 within each hospital room 80, 82, 84, 86, 88, 90 and 92. Each station distributing means 20 modulates each variable monitoring signal it receives and combines the modulated signal components to form a mixed signal therefrom. The mixed signal further includes an operator input routing signal and/or source identifier. The routing signal and/or source identifier may be input to the station monitoring means 20 via a keyboard 36. The mixed signal is transmitted via existing telephone lines 81, 83, 85, 87, 89, 91 and 93 to a system distributing means 50 which is connected in parallel to a telephone switching system 55 within the hospital which services the telephones in each of the seven hospital rooms. As shown in FIG. 1, the telephone switching system is connected to a telephone central office 65 for outgoing calls as well as to telephones 102, 103, 104, 105 connected through the system monitoring devices. Telephone voice communication from/to telephones coupled to each of the station distributing means or system monitoring devices may be present on the telephone lines without being interrupted or interfered with by the mixed signals which are carried over the telephone lines outside the audio range. More specifically, the transmission of the information over the pre-existing telephone lines is designed so that it does not create an off-hook situation. The only off-hook situation is created by actual use of the telephones by patients and/or visitors making normal telephone calls. In this way, normal telephone operation continues uninterrupted regardless of the transmission of medical information over the telephone line from a station distributing means to a system distributing means.

As discussed above, the system distributing means 50 demodulates each mixed signal received from each station distributing means 20. Components of the demodulated mixed signal are separated and based upon the routing and/or source identifying information within the mixed signal, the mixed signal components are selectively distributed to each or any of four system monitoring apparatus, 94, 96, 98 and 100, designated A, B, C, D, respectively. System monitoring devices A, B, C, D correspond to each medical monitoring apparatus A, B, C, D. In one particular distribution scenario, the component signals received from each of the seven medical monitoring apparatus A at each of the seven hospital rooms are distributed by system distributing means 50 to system monitoring apparatus 94 (designated A in FIG. 2) based upon a specific routing signal provided by the operator at the station monitoring means. System monitoring apparatus A receives each of the seven component signals for either display or further processing.

Similarly, if the routing signal input by the operator so designates, the system distributing means 50 distributes each of the seven component signals generated within each of medical monitor apparatus B, C and D, respectively, at each of the seven hospital rooms to system monitoring apparatus 96, 98 and 100, respectively (designated B, C and D in FIG. 2). Each system monitoring device A, B, C, D may therefore monitor the condition of seven patients present within each of the seven hospital rooms concurrently, using the existing telephone lines. The continuous medical monitoring system 78 of the present invention avoids the need for locating seven corresponding sets of four electrical wires or cables corresponding to A, B, C, D between the seven hospital rooms and the four system monitoring devices. Alternatively, the medical information may be distributed such that all monitoring information from a particular room may be provided to a single central system monitoring device. In this way, several of a patient's physical parameters may be monitored by a doctor at a single remote location, i.e., an office within the hospital or an office outside the hospital setting. Thus, the medical monitoring information is capable of being selectively distributed in any combination of ways to multiple targets, i.e., system monitoring devices, located in a variety of places.

Figure 3:
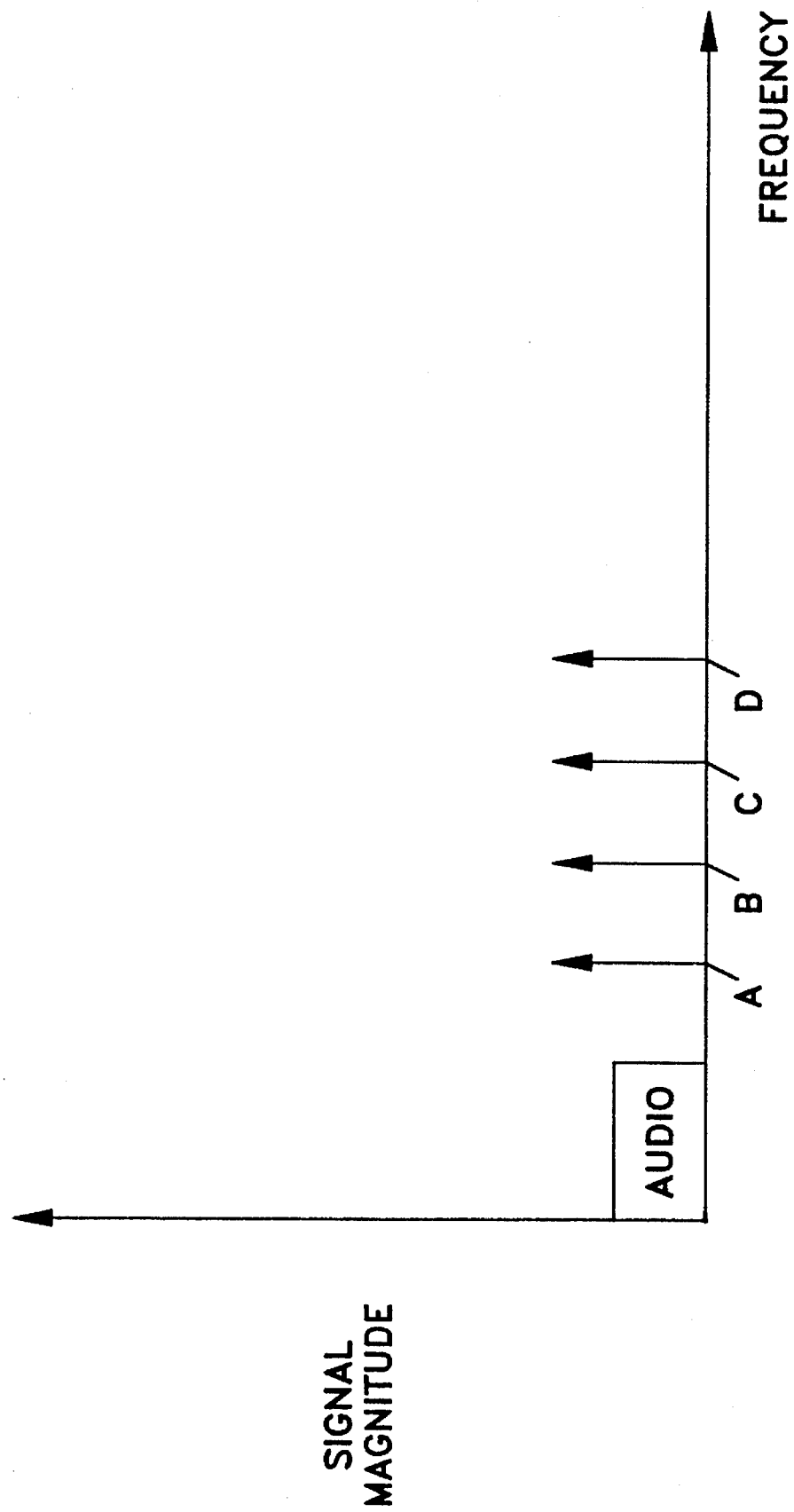
FIG. 3 is spectrum analysis plot showing several possible frequency locations of monitoring signal components within a mixed signal of the present invention.

FIG. 3 shows a spectrum analysis plot of a typical mixed signal which may be generated within a station distributing means 20 of the present invention. The audio baseband is designated in FIG. 3 as well as spectral lines A, B, C and D. The audio baseband corresponds to that frequency bandwidth containing frequencies audible by the human ear. In one particular embodiment, spectral lines A, B, C, D correspond to the frequencies of the modulated components resulting from the modulation of the variable monitoring signals generated within medical monitoring apparatus A, B, C, D. Because each of the four spectral lines (i.e., frequencies) corresponding to the four variable monitoring signals extend beyond the audio baseband, their presence on a telephone line will be transparent to a telephone user. Furthermore, as noted above, since the spectral lines for the monitoring apparatus are shown at different frequencies, it is possible to separate and distribute the components of the mixed signal based upon the varying frequencies to any number of system monitoring devices.

In an alternative embodiment, the mixed signal may be formed as a digital signal for transmission over a preexisting telephone line. The digital signal may be formed from the medical monitoring apparatus in the form of binary digits in the station distributing means by an analog-to-digital converter. The monitoring information is preferably encoded with a binary code to distinguish each monitoring apparatus from one another. This digital signal transmission is especially well suited for use with an Integrated Services Digital Network (ISDN). Should the digital information be transmitted to conventional analog receivers, it will be necessary to convert the digital bit stream to an analog signal using a digital-to-analog converter.

The encoded digital mixed signal formed by the station monitoring means is received at the system distributing means via a pre-existing telephone line. The system distributing means can separate the components of the mixed signal based upon the encoded information which forms a part of the monitoring apparatus signal, so that the system distributing means can route the separated components of the mixed signal to the desired system monitoring apparatus.

Figure 4:
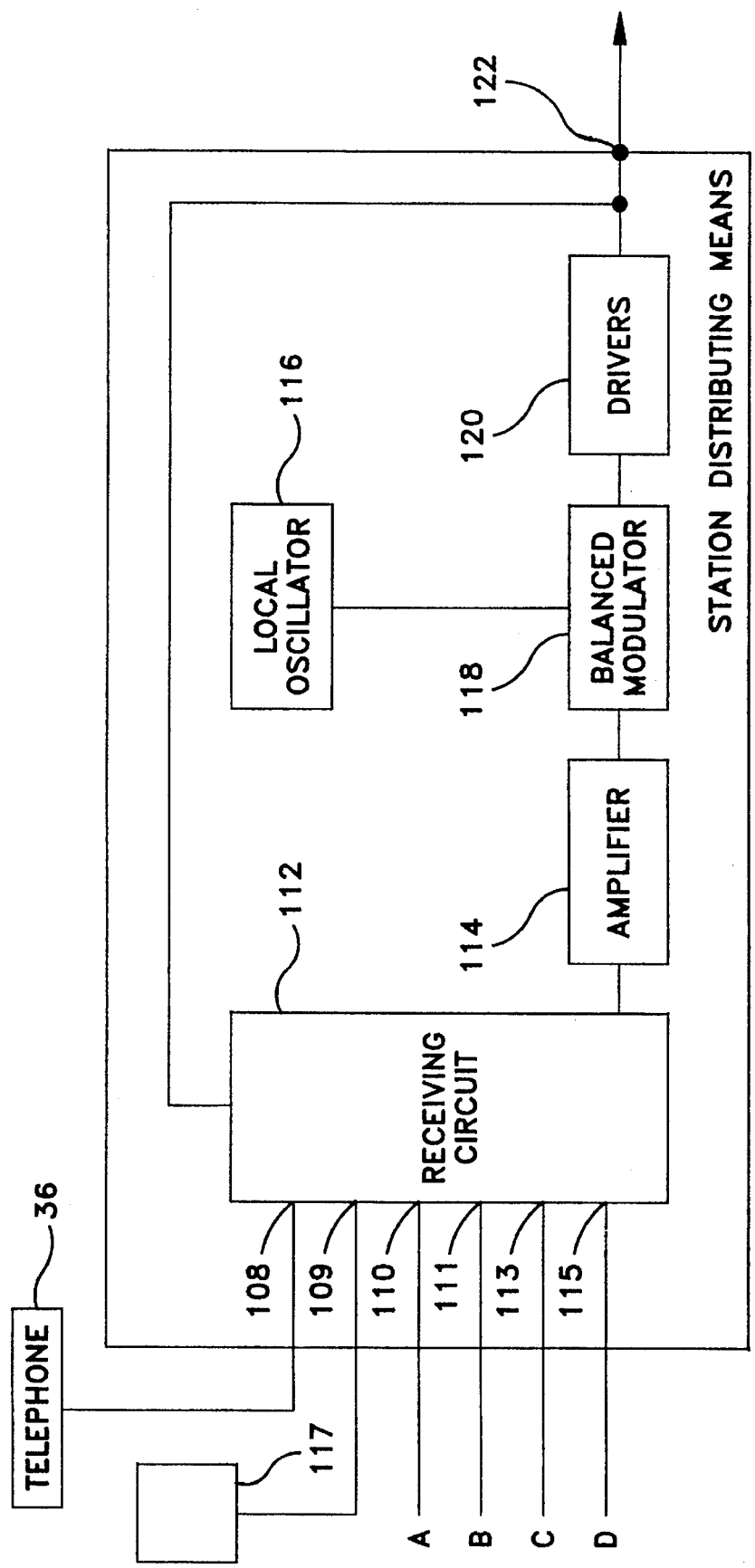
FIG. 4 is a detailed block diagram of a station distributing means of the present invention.

FIG. 4 shows a schematic block diagram of one embodiment of a station distributing means 20 of the present invention. Each variable monitoring signal generated within each medical monitoring apparatus A, B, C, D is electrically coupled to a receiving circuit 112 within station distributing means 20 through ports 110, 111, 113 and 115, respectively. Receiving circuit 112 directs the variable monitoring signals to an amplifier circuit 114, where the signals are adjusted to proper signal levels. The adjusted monitoring signals are then passed to a balanced modulator 118 for modulation by a local oscillator 116. The modulated output, i.e., the mixed information signal, is then provided to driver 120. Driver 120 amplifies the mixed signal's power level as needed before the mixed signal is transmitted over a telephone line.

FIG. 4 also shows a telephone 36 electrically connected at port 108 to station distributing means 20. The voice communication signal generated within telephone 36 may be transferred through the receiving circuit for output directly onto the telephone line via port 122. Port 109 is designated to receive data input from a computer, a keyboard or other data inputting device 117. The data input device 117 may also be used to encode the mixed signal to provide routing and source identity information, such as a telephone exchange or a code corresponding to a specific system monitoring apparatus location. Alternatively, the data input device may be used to provide data to a system monitoring apparatus (72, 70 of FIG. 1). Once data is input to the station distributing means 20, the data is modulated and incorporated within the mixed information signal for transmission. System distributing means 50 (FIG. 1) demodulates and retrieves the modulated data signal component from the mixed information signal and directs the components to its appropriate destination.

Figure 5:
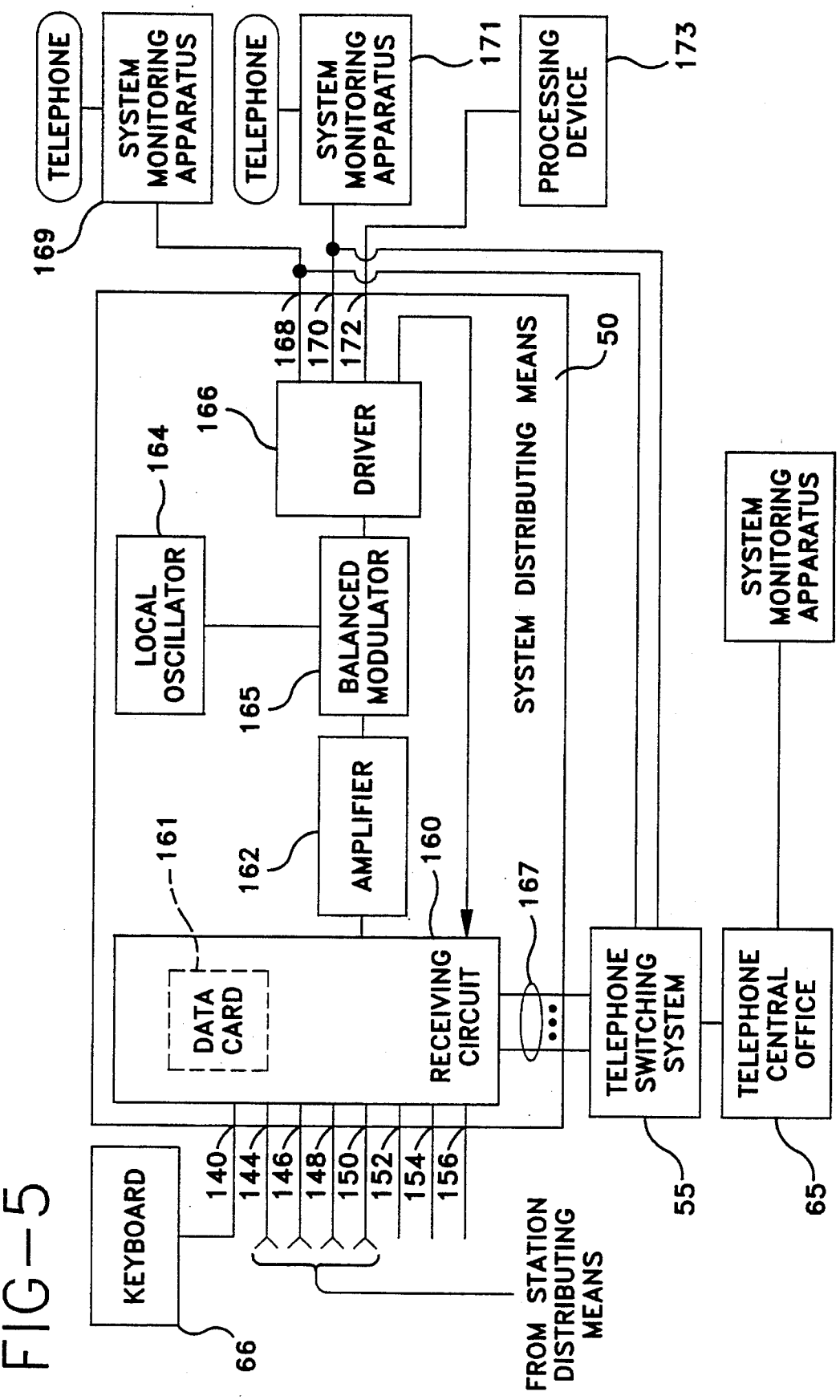
FIG. 5 is a detailed block diagram of a system distributing means of the present invention.

FIG. 5 shows a block diagram of one embodiment of a system distributing means 50 of the present invention. System distributing means 50 receives input from telephone lines or data input devices through input jacks (not shown) at any of even numbered ports 140–156. Ports 144, 146, 148, and 150 are electrically connected via existing telephone lines to four station distributing means 20 (FIG. 2) for receiving mixed information signals therefrom. Also, normal telephone signals may be received by the system distribution means 50 for normal routing through a telephone switching system. These signals are permitted to pass transparently through the system distribution means without interruption via lines 40', 42' and 44' to the telephone switching system 55. Port 140 may receive data input from a keyboard or other user initiated data inputting device.

All mixed information signals received within system distributing means 50 are first processed at receiving circuit 160. More specifically, the system distributing means is preferably a parallel connected apparatus with the telephone switching system 55, which is in turn coupled to a telephone central office. The parallel connections of the telephone lines is shown in FIG. 5 as reference numeral 167. For example, in a hospital setting, the hospital building may include a central switching system, such as a Private Branch Exchange (PBX) for analog signals or an Integrated Services Digital Network (ISDN) for a digital signal telephone network.

As previously noted, the system distributing means 50 includes a receiving circuit 160. In the case of a hospital setting, the telephone lines coupled to the station distributing means converge at the central telephone switching system. The system distributing means is parallel connected to the incoming telephone lines near the central telephone switching system. The receiving circuit 160, which receives all the information from each of the station distributing means, includes a data card which is pre-programmed to process, prioritize and direct the components of the mixed signals based upon the routing information contained therein.

For example, the routing information contained in the mixed signal from a plurality of station distributing means may provide that all the information be directed to a central system monitoring apparatus located within the hospital. Such routing information may be in the form of a four digit telephone number to direct the information to a system monitoring apparatus coupled to a telephone jack within the hospital. Alternatively, the routing information may include a telephone exchange, i.e., a seven digit code, such that the system distributing means converts the information to an in-base band signal which is provided to the telephone switching system for transmission to a central office, and ultimately to be received by a local outside system monitoring apparatus. Alternatively, the signal may be directed to a Private Automatic Branch Exchange (PABX) for routing to a system monitoring apparatus located outside the hospital setting, e.g., a doctor's office. The routing information may also be a ten digit code to provide the medical monitoring information over a long distance phone line to a remote system monitoring apparatus. It should be noted that the duplicate connections from the telephone switching system and system distributing means in the telephone lines coupled to the system monitoring devices may not be required. For example, should all information be sorted and then distributed by a telephone exchange, the information could be provided to the system monitoring of these devices via the telephone switching network. On the other hand, those of ordinary skill in the art may find it useful to have the duplicate connections so that the system distributing means provides the output signals to the system monitoring apparatus.

The telephone switching system and data card shall be configured to allow normal telephone usage during the transmission of the mixed signal from the station monitoring means to the system monitoring means. More specifically, the patient will still be able to make and receive telephone calls, uninterrupted by the information signal which is transmitted outside the audio base-band. This is possible since transmission of data does not provide an off-hook situation. Only usage of the telephone distribution means produces an off-hook situation. The usage of the telephone also does not affect the transmission of the medical monitoring information.

In one embodiment, the data card is programmed to monitor all signals being sent to a central telephone switching system for detection of any out of audio base-band signals. Upon detection of the signals, the system distributing means is capable of sorting these signals, decoding routing information, and directing the signals to an appropriate system monitoring apparatus. Data cards of this nature are well known within the telephone industry, and those skilled in the art will recognize that the data card may be easily programmed to accomplish the functions described above.

Referring to FIG. 5, the receiving circuit 160 distributes the signals to an amplifier circuit 162. Amplifier circuit 162 adjusts the levels of the received signals and transfers the same to a balanced modulator 165. The mixed signals are demodulated, if required, within balanced modulator 165 using signals generated by local oscillator 164. As previously discussed, signal components which have been separated from the mixed signals are distributed as provided by the routing information via driver 166 to the appropriate system monitoring apparatus 169, 171, processing device 173, or telephone central office electrically coupled through ports 168, 170, 172, and 174 respectively.

Internally, an electrical connection is provided within system distributing means 50 from driver 166 back to receiving circuit 160. The electrical connection transfers a data signal, formed by modulating data input via port 140 for transfer to receiver circuit 160. Receiver circuit 160 routes the modulated data signal over an appropriate telephone line or lines to the appropriate station distributing means 20. Accordingly, two-way communication of medical monitoring and user information may be implemented using existing telephone lines without interrupting normal telephone communication on the telephone line.

It should be noted that the specific embodiments of the medical monitoring system identified in this disclosure may be replaced by other means without materially affecting the invention to transmit information over an existing telephone line without disturbing telephone communications thereon. The invention accordingly is not limited to the precise embodiments disclosed, and various other changes and modifications may be affected therein by one skilled in the art without departing from the scope or spirit of the invention.

I claim:

1. A medical monitoring system, comprising:
   - at least one patient medical monitoring apparatus for monitoring at least one aspect of a patient's physical condition and generating at least one real-time variable signal in response thereto;
   - at least one station distributing means electrically connected to said at least one patient medical monitoring apparatus, the station distributing means being electrically coupled to a first end of a telephone line;
   - a system distributing means electrically connected to a second end of said telephone line; and
   - at least one system monitoring apparatus electrically connected to said system distributing means;

wherein said at least one station distributing means receives each of said at least one variable signal, and generates an information signal therefrom, the station distributing means including means for encoding the information signal to include routing information therein and means for modulating the encoded information signal to a frequency outside an audio baseband, wherein said station distributing means transmits the encoded information signal over said telephone line to said system distributing means, wherein the system distributing means includes a means for sorting, prioritizing and directing the information signal based upon the routing information contained therein, the system distributing means directing the information contained therein to said at least one system monitoring apparatus, whereby transmission of said information signal does not affect normal telephone operation.

2. A medical monitoring system as defined by claim 1, wherein said variable signal is a continuous variable signal.

3. A medical monitoring system as defined by claim 1, wherein said at least one station distributing means includes means for modulating said at least one variable signal to form said information signal, and wherein said system distributing means includes means to demodulate said information signal into separate signal components.

4. A medical monitoring system as defined by claim 1, further comprising at least one telephone electrically connected to said at least one station distributing means for normal telephone communication.

5. A medical monitoring system as defined by claim 1, wherein the sorting, prioritizing and directing means comprises a programmed data card further comprising at least one telephone electrically connected to the system distributing means for normal telephone communication.

6. A medical monitoring system as defined by claim 1, wherein said encoding means comprises a keyboard or the like.

7. A medical monitoring system as defined by claim 1, wherein said system monitoring apparatus includes one of a data display, a microcomputer with display, a facsimile device, a modem and a memory device.

8. A medical monitoring system as defined by claim 1, wherein the information signal includes a plurality of components, and further wherein the system distributing means can selectively direct each of the components of the information signal to any of a plurality of system monitoring apparatus.

9. A method of monitoring a patient's condition, comprising the steps of:

applying at least one medical monitoring device to the patient;

generating a monitoring signal from the at least one medical monitoring device;

generating a routing signal from a user input device;

combining the monitoring signal and routing signal in a station distributing means to form a mixed information signal;

modulating the mixed information signal to a frequency outside the audio baseband;

transmitting the mixed information signal over an existing telephone line to a system distribution means;

receiving the mixed information signal by the system distributing means;

sorting, prioritizing and directing the mixed information signal based upon the routing information contained therein to at least one system monitoring apparatus; and displaying the mixed information signal at the at least one system monitoring apparatus to provide real-time monitoring information to a remote location, and wherein normal telephone operation is not interrupted during transmission of the mixed information signal at the frequency outside the audio baseband.

10. A method as defined by claim 9, further comprising the steps of:

converting the mixed information signal received by the system distributing means into an in audio baseband signal; and transmitting the audio in baseband mixed information signal via a telephone network to a remote system monitoring apparatus.

11. A method as defined by claim 9, wherein the step of sorting, prioritizing and directing includes selectively directing any number of monitoring signals to any of a plurality of system monitoring apparatus.

12. A medical monitoring system for use within a hospital setting, comprising:

at least one patient medical monitoring apparatus for monitoring at least one aspect of a patient's physical condition and generating at least one real-time variable signal in response thereto;

at least one station distributing means having an input electrically connected to said at least one patient medical monitoring apparatus, the station distributing means having an output being electrically coupled to a first end of a telephone line;

a system distributing means having an input electrically connected to a second end of said telephone line; and at least one system monitoring apparatus electrically connected to an output of said system distributing means;

wherein said at least one station distributing means receives each of said at least one variable signals and generates an information signal therefrom, the station distributing means including means for modulating the information signal to a frequency outside an audio baseband, wherein said station distributing means transmits the modulated information signal over said telephone line to said system distributing means, wherein the system distributing means includes a means for detecting and demodulating the information signal, the system distributing means further including preprogrammed directing means for directing the information contained therein to said at least one system monitoring apparatus, whereby transmission of said information signal does not affect normal telephone operation.

13. A medical monitoring system as defined by claim 12, wherein a plurality of medical monitoring apparatus each form a component of the information signal and wherein the preprogrammed directing means of the system distributing means is capable of selectively directing each component of the information signal to any of a plurality of system monitoring apparatus.

14. A medical monitoring system as defined by claim 13, wherein the preprogrammed directing means of the system distributing means is a data card.

15. A medical monitoring system as defined by claim 12, wherein the station distributing means further comprises a means for encoding the information signal to include routing information for directing the information signal to any of the at least one system monitoring apparatus.

16. A medical monitoring system as defined by claim 15, wherein the routing information is in the form of one of a four digit, seven digit and ten digit code.

17. A medical monitoring system as defined by claim 16, wherein the four digit code directs the information signal to a system monitoring apparatus within the hospital; and wherein the seven and ten digit codes direct the information signal to a telephone switching system for transmission to a system monitoring device either locally outside or a long distance from the hospital, respectively.

18. A medical monitoring system as defined by claim 12, further comprising at least one telephone electrically connected to said at least one station distributing means for normal telephone communication.

19. A medical monitoring system as defined by claim 12, wherein the system monitoring apparatus includes one of a data display, a microcomputer with a display, a facsimile device, a modem and a memory device.

20. A medical monitoring system as defined by claim 12, wherein the detecting means recognizes only out of audio baseband signals and is transparent to normal telephone communication signals.

* * * * *

UNITED STATES PATENT AND TRADEMARK OFFICE
CERTIFICATE OF CORRECTION

PATENT NO. : 5,579,378

DATED : November 26, 1996

INVENTOR(S) : Frank H. Arlinghaus, Jr.,

It is certified that error appears in the above-identified patent and that said Letters Patent is hereby corrected as shown below:

On the title page, showing the illustrative figure 1, should be deleted and substitute therefor the attached title page.

The drawing sheet consisting of Fig 1, should be deleted and replaced with the drawing sheet, consisting of Fig. 1.

In Column 6, Line 42,     delete "36" and insert therefor --32--.

United States Patent [19]

Arlinghaus, Jr.

[11] Patent Number: 5,579,378
[45] Date of Patent: Nov. 26, 1996

[54] MEDICAL MONITORING SYSTEM

[76] Inventor: Frank H. Arlinghaus, Jr., Windmill La., Rumson, N.J. 07760

[21] Appl. No.: 533,167

[22] Filed: Sep. 25, 1995

Related U.S. Application Data

[63] Continuation-in-part of Ser. No. 111,630, Aug. 25, 1993, abandoned.

[51] Int. Cl.⁶ .................................................. H04M 11/00
[52] U.S. Cl. .................. 379/106; 379/90; 364/413.02; 128/904
[58] Field of Search .......................... 379/38, 45, 49, 379/42, 52, 106, 107, 102, 104, 93, 97–99; 128/670, 904; 395/500; 364/413.02

[56] References Cited

U.S. PATENT DOCUMENTS

| | | |
|---|---|---|
| 3,726,270 | 4/1973 | Griffis et al. . |
| 3,872,253 | 3/1975 | Jurschak . |
| 3,896,792 | 7/1975 | Vail et al. . |
| 4,006,461 | 2/1977 | Coulter et al. . |
| 4,034,743 | 7/1977 | Greenwood et al. . |
| 4,296,756 | 10/1981 | Dunning et al. . |
| 4,528,422 | 7/1985 | Cupani . |
| 4,531,527 | 7/1985 | Reinhold . |
| 4,608,686 | 8/1986 | Barsellotti . |
| 4,685,123 | 8/1987 | Hsia et al. . |
| 4,741,022 | 4/1988 | Chebra et al. . |
| 4,838,275 | 6/1989 | Lee . |
| 5,161,222 | 11/1992 | Montejo . |
| 5,369,691 | 11/1994 | Cain et al. . |

*Primary Examiner*—Wing F. Chan
*Attorney, Agent, or Firm*—Hoffmann & Baron

[57] ABSTRACT

A medical monitoring system which includes at least one patient medical monitoring apparatus for monitoring at least one aspect of a patient's physical condition and generating at least one variable signal in response to the monitoring. The system includes at least one station distributor electrically connected to the at least one patient medical monitoring apparatus and to a first end of a telephone line. A system distributor is electrically connected to a second end of a telephone line and to at least one system monitoring apparatus. The at least one station distributor receives each of the at least one variable signals and generates an information signal therefrom. The information signal is transmitted to the system distributor where monitoring information contained within the information signal is retrieved and distributed to the at least one system monitoring apparatus without interrupting normal telephone operation.

20 Claims, 5 Drawing Sheets

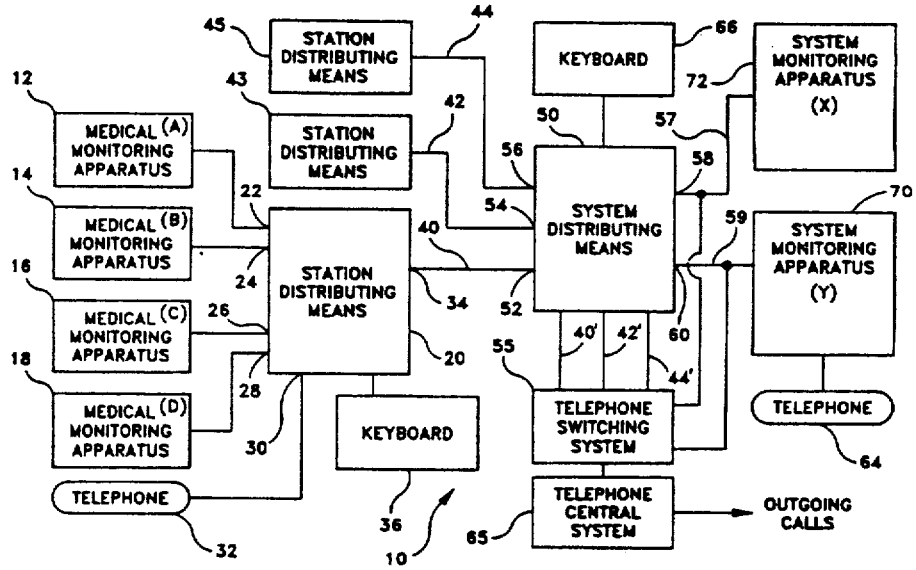

UNITED STATES PATENT AND TRADEMARK OFFICE
CERTIFICATE OF CORRECTION

Page 3 of 3

PATENT NO. : 5,579,378
DATED : November 26, 1996
INVENTOR(S) : Frank H. Arlinghaus, Jr.

It is certified that error appears in the above-indentified patent and that said Letters Patent is hereby corrected as shown below:

The drawing on the title page and Figure 1 located on sheet 1 should appear as follows:

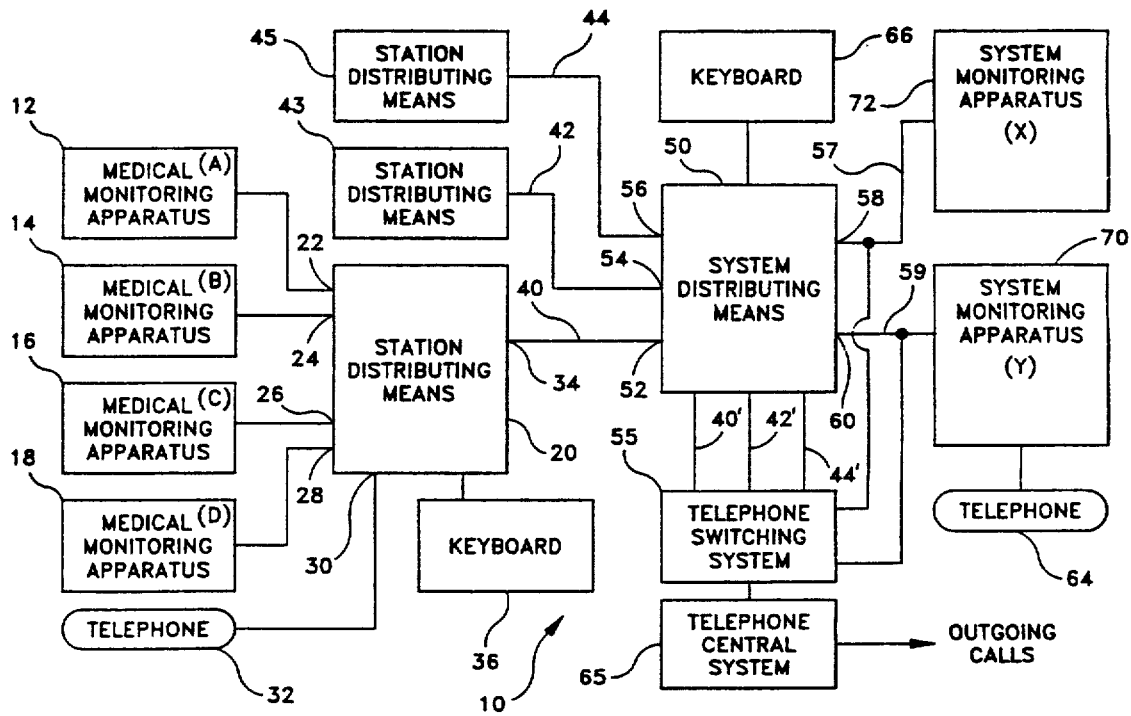

In Column 6, Line 42,   delete "36" and insert therefor --32--.

Signed and Sealed this

Third Day of June, 1997

Attest:

BRUCE LEHMAN

Attesting Officer

Commissioner of Patents and Trademarks